United States Patent [19]
Mewshaw et al.

[11] Patent Number: 5,958,965
[45] Date of Patent: Sep. 28, 1999

[54] 4-AMINOETHOXY INDOLES

[75] Inventors: Richard Eric Mewshaw, Princeton, N.J.; Michael Byron Webb, Levittown, Pa.

[73] Assignee: American Home Products Corporation, Madison, N.J.

[21] Appl. No.: 08/909,803

[22] Filed: Aug. 12, 1997

Related U.S. Application Data

[60] Provisional application No. 60/024,636, Aug. 27, 1996.

[51] Int. Cl.⁶ .......................... A01N 43/38; C07D 209/04
[52] U.S. Cl. ........................ 514/415; 548/490; 548/491
[58] Field of Search ........................... 514/415; 348/490, 348/491

[56] References Cited

U.S. PATENT DOCUMENTS

| | | | |
|---|---|---|---|
| 3,904,645 | 9/1975 | McManus | 260/326.5 |
| 3,906,000 | 9/1975 | McManus | 260/326.5 |
| 5,013,761 | 5/1991 | Beedle et al. | 514/650 |
| 5,541,199 | 7/1996 | Mewshaw | 514/314 |
| 5,552,429 | 9/1996 | Wong et al. | 514/415 |
| 5,627,196 | 5/1997 | Audia et al. | 514/323 |

FOREIGN PATENT DOCUMENTS 25558   1/1966   France .

OTHER PUBLICATIONS

Corsini et al., Adv. Biochem. Psychopharmacol 16, 645–648 (1977).
Tamminga et al. Science, 200, 567–568 (1978).
Tamminga et al., Arch. Gen. Psychiatry, 43, 398–402 (1986).
Lahti et al., Mol. Pharma. 42, 432–438 (1993).
Hosohata et al., "A non–selective beta–blocker, bopindolol, exhibits high affinity to 5–HT1A receptor subtype in rat brain as assayed by competition binding experiments", Biogenic Amines, vol. 12, No. 3. pp. 253–258, 1996.

*Primary Examiner*—Dwayne C. Jones
*Attorney, Agent, or Firm*—Rebecca R. Barrett

[57] ABSTRACT

Compounds of the formula:

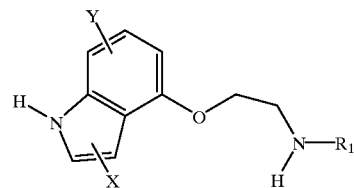

in which $R_1$ is hydrogen, alkyl, cycloalkylalkyl, arylalkyl, (haloaryl)alkyl, (alkoxyaryl)alkyl, thienylmethyl, furanylmethyl, pyridinylmethyl, alkylphenyl, 4-fluorobutyrophenone or 6-fluoro-1,2-benzisoxazol-yl-propyl; X is hydrogen, halogen, cyano, alkyl, acetyl, trifluoroacetyl, trifluoromethyl or formyl; Y is hydrogen, halogen, alkoxy or alkyl; or a pharmaceutically acceptable salt thereof are inhibitors of dopamine synthesis and release, useful in the treatment of schizophrenia, Parkinson's Disease, Tourette's Syndrome, alcohol addiction, cocaine addiction, and addiction to analagous drugs and they also have affinity for the 5-$HT_{1A}$ receptors which characterizes them as useful in the treatment of diseases attending disturbances in the serotinergic systems, such as anxiety, stress, depression, sexual dysfunctions and sleep disturbances.

15 Claims, No Drawings

4-AMINOETHOXY INDOLES

This application claims the benefit of U.S. Provisional Application No. 60/024,636 filed Aug. 27, 1996.

BACKGROUND OF INVENTION

Efforts to induce antipsychotic activity with dopamine autoreceptor agonists have been successful [Dorsini et al., Adv. Biochem. Psychopharmacol 16, 645–648, (1977); Tamminga et al., Science 200, 567–568; and Tamminga et al., Psychiatry 398–402, (1986)]. A method for determining intrinsic activity at the dopamine $D_2$ receptor was recently reported [Lahti et al., Mol. Pharrn. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist and antagonist activities of a given compound, which activities characterize a compound's ability to elicit an antipsychotic effect.

U.S. Pat. Nos. 3,906,000 and 3,904,645 describe a series of indoles which are useful as oral hypoglycemic agents. Troxler et al. 66-25558F: WPIDS describes a series of indoles including 4-(2-hydroxy-3-isopropyl- or secondary butyl-amino-propoxy)-indoles which are useful as β-adrenergic blocking agents for the treatment of heart diseases.

DESCRIPTION OF THE INVENTION

In accordance with this invention, there is provided a group of aminoethoxy indole derivatives which are useful antipsychotic agents. In addition, this invention provides processes for preparation of the compounds and methods for their use in treating diseases of the central nervous system. The aminoethoxy indoles of ths invention are illustrated by the following Formula I:

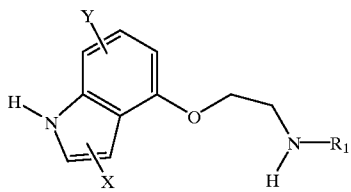

in which:

$R_1$ is hydrogen, alkyl of 1 to 10 carbon atoms, cycloalkylalkyl of 6 to 12 carbon atoms, arylalkyl of 7 to 12 carbon atoms, (haloaryl)alkyl of 7 to 12 carbon atoms, (alkoxyaryl) alkyl of 8 to 12 carbon atoms, thienylmethyl, furanylmethyl, pyridinylmethyl, alkylphenyl of 7 to 12 carbon atoms, 4-fluorobutyrophenone or 6-fluoro-1,2-benzisoxazol-yl-propyl;

X is hydrogen, halogen, cyano, alkyl of 1 to 6 carbon atoms, acetyl, trifluoroacetyl, trifluoromethyl or formyl;

Y is hydrogen, halogen, alkoxy of 1 to 6 carbon atoms or alkyl of 1 to 6 carbon atoms;

or a pharmaceutically acceptable salt thereof

More specifically, the compounds of this invention are 4-aminoethoxy-indoles illustrated by Formula I.

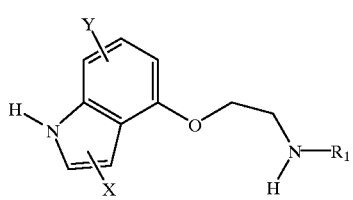

in which:

$R_1$ is hydrogen, alkyl of 1 to 10 carbon atoms, cyclohexylmethyl, arylalkyl of 7 to 12 carbon atoms, (haloaryl)alkyl of 7 to 12 carbon atoms or (alkoxyaryl)alkyl of 8 to 12 carbon atoms;

X is hydrogen, halogen, cyano, alkyl of 1 to 6 carbon atoms, acetyl, trifluoroacetyl, trifluoromethyl or formyl;

Y is hydrogen, halogen, alkoxy of 1 to 6 carbon atoms or alkyl of 1 to 6 carbon atoms;

or a pharmaceutically acceptable salt thereof.

More preferred compounds are those of Formula I in which $R_1$ is alkyl of 1 to 6 carbon atoms, benzyl, halobenzyl, alkoxybenzyl of 8 to 12 carbon atoms or alkylbenzyl of 8 to 12 carbon atoms; X is hydrogen, halogen or trifluoroacetyl and Y is hydrogen or halogen; or a pharmaceutically acceptable salt thereof.

The pharmaceutically acceptable acids from which addition salts are conventionally produced, having the same utility as the free base, include both inorganic or organic acids. For example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric, nitric acid, and the like, are suitable for this purpose.

The compounds of Formula I are generally prepared by the overall reaction sequence indicated in Schemes I, II and III as follows:

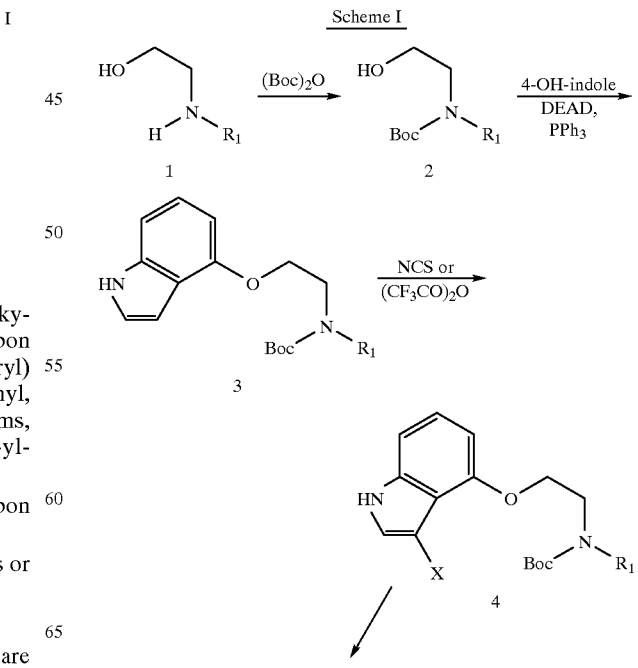

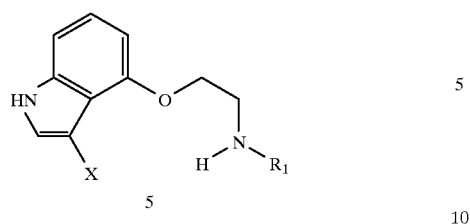
Scheme II
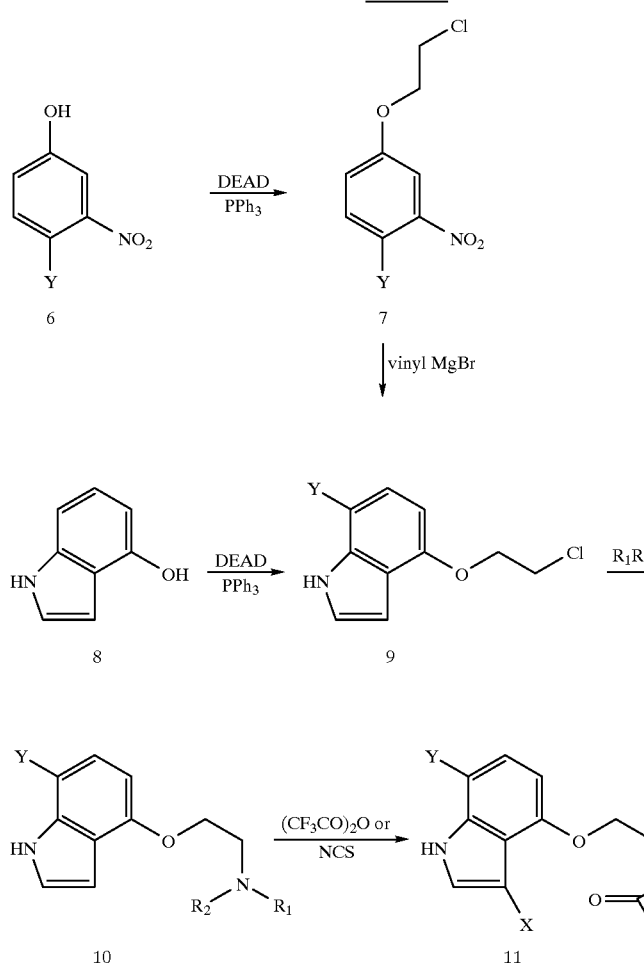
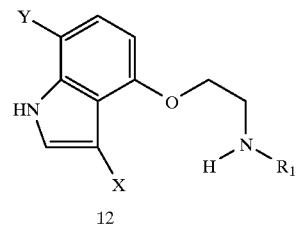

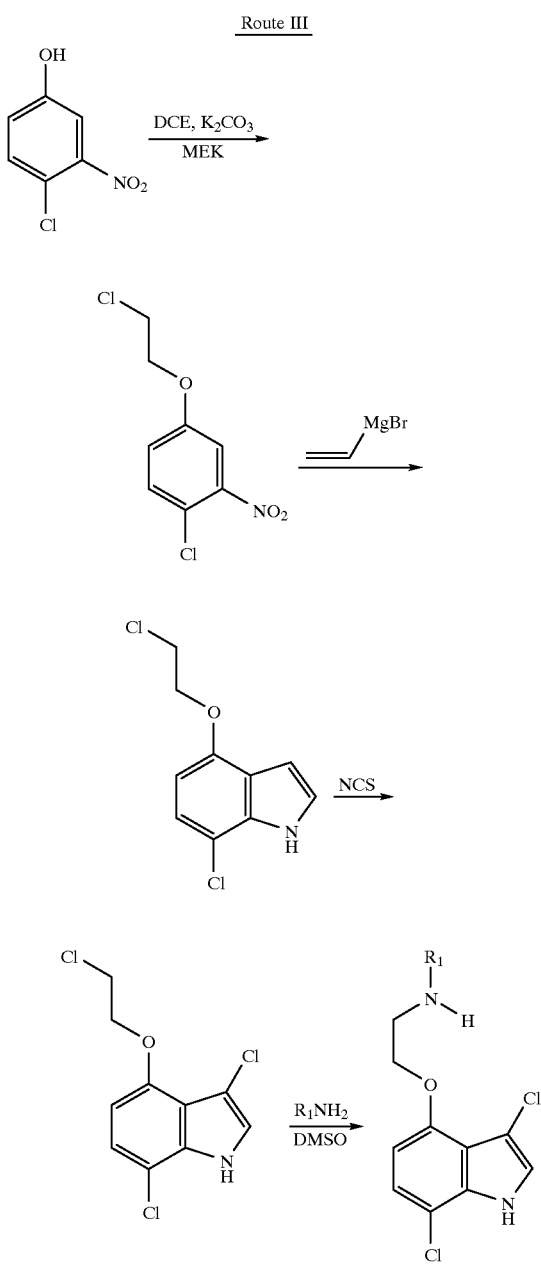

Scheme III

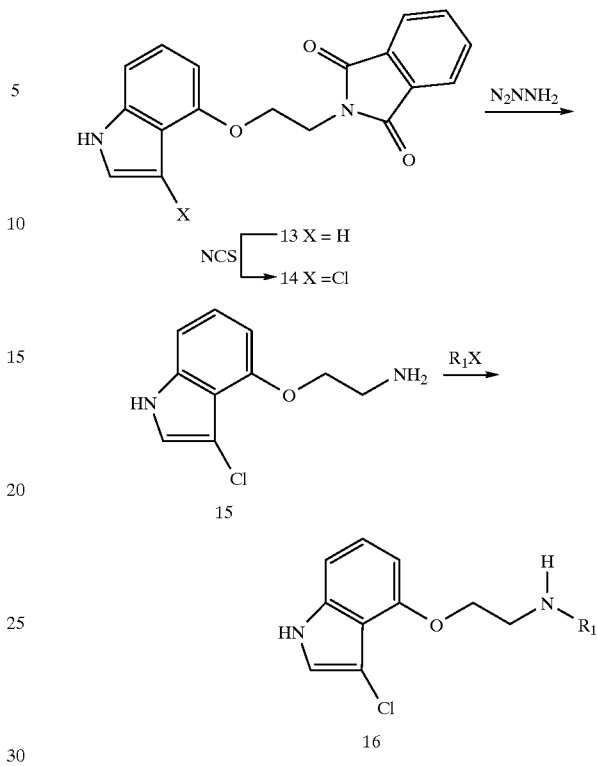

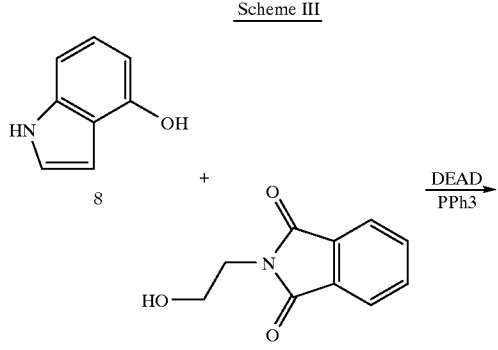

The compounds of this invention are dopamine agonists with various degrees of intrinsic activity. Some are selective autoreceptor agonists and others bind to the postsynaptic $D_2$ receptors. The autoreceptor agonists act as partial agonists (i.e. activate only autoreceptors versus postsynaptic $D_2$ dopamine receptors). As such, they provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia. Activation of the dopamine autoreceptors results in reduced neuronal firing as well as inhibition of dopamine synthesis and release and therefore provide a means of controlling hyperactivity of the dopaminergic systems with essentially no extrapyramidal side effects (EPS).

The compounds of this invention were also found to have affinity for the $5\text{-HT}_{1A}$ receptors and therefore have the ability to modulate serotonergic activity. As such, they are useful in the treatment of diseases characterized by disturbances in the dopaminergic and serotinergic systems, such as schizophrenia, Parkinson's disease, Tourette's Syndrome, alcohol addiction, cocaine addiction, anxiety, stress, depression, sexual dysfunctions and sleep disturbances.

The following examples illustrate, without limitation, methods for production of the compounds of this invention.

Intermediate 1

N-Benzyl-N-(2-hydroxy-ethyl)-carbamic acid tert-butyl ester

A solution of N-benzylaminoethanol (4.8 g, 31.9 mmol) and di-tertbutyl-dicarbonate (7.5 g, 34.4 mmol) in anhydrous tetrahydrofuran (30 mL) was stirred at ambient temperature for 18 hours. The solvent was removed and the product purified by flash chromatography (ethyl acetate-hexane, 1:1) to afford 8.0 g (99%) of a thick oil.

Elemental analysis for $C_{14}H_{21}NO_3$
Calc'd: C, 66.91; H, 8.42; N, 5.57
Found: C, 66.64; H, 8.59; N, 5.60

This general procedure utilizing N-methylaminoethanol afforded:
(1b) N-Methyl-N-(2-hydroxy-ethyl)-carbamic acid tert-butyl ester as a clear oil (83.7%); MS m/z 175 (M+).
Elemental analysis for $C_8H_{17}NO_3$
Calc'd C, 54.84; H, 9.78; N, 7.99
Found C, 54.35; H, 10.00; N, 7.84

Intermediate 2

Method A

N-Benzyl-N-[2-(1H-indol-4-yloxy)-ethyl]-carbamic acid tert-butyl ester

To a solution of benzyl-(2-hydroxy-ethyl)-carbamic acid tert-butyl ester (12.68 g, 50.5 mmol), 4-hydroxyindole (4.48 g, 33.6 mmol) and triphenylphosphine (14.1 g, 53.8 mmol) in anhydrous tetrahydrofuran (130 mL) was slowly added a solution of diethylazidocarboxylate (9.38 g, 53.8 mmol) in tetrahydrofuran (15 mL) at room temperature. The reaction mixture was stirred for 16 hours and then the solvent was removed and the crude product dissolved in diethyl ether and diluted with hexanes. After standing for 30 minutes, the solid was filtered and the filtrate concentrated. The product was purified by flash chromatography to afford 8.6 g of a yellow oil (69.7%).
Elemental analysis for $C_{22}H_{26}N_2O_3$
Calc'd: C, 72.11; H, 7.15; N, 7.64
Found: C, 71.39; H, 7.28; N, 7.21

This general procedure utilizing N-methyl-N-(2-hydroxy-ethyl)-carbamic acid tert-butyl ester, N-(2-hydroxyethyl)-phthalimide afforded, chloroethanol or 4-chloro-3-nitrophenol afforded, respectively:
(2b) N-Methyl-N-[2-(1H-indol-4-yloxy)-ethyl]-carbamic acid tert-butyl ester as a yellow oil; (77.2%); MS EI m/z 290 (M+).
(2c) N-[2-(1H-Indol-4-yloxy)-ethyl]-phthalimide as a white solid: (13.2%); mp 155–157° C.; IR (KBr) 3400, 1725 cm-1; MS EI m/e 306 (M+).
Elemental analysis for $C_{18}H_{14}N_2O_3$
Calc'd: C, 70.58; H, 4.61; N, 9.15.
Found: C, 70.33; H, 4.43; N, 9.11.
(2d) 2-(1H-Indol-4-yloxy)-chloroethane: (57%), mp 62–63° C.
(2e) 1-(2-Chloroethoxy)-4-chloro-3-nitrobenzene: (93%); mp 46–48° C.; MS EI m/e 235, 237, 239 (M+); $^1$H NMR (400 MHz, DMSO-$d_6$) δ 3.95 (t, 2H, J=5.2 Hz), 4.36 (t, 2H, J=5.2 Hz), 7.32 (dd, 1H, J=3.2, J=8.9 Hz), 7.66, (d, 1H, J=9 Hz), 7.69, (d, 1H, J=3.2 Hz).
Elemental analysis for $C_8H_7Cl_2NO_3$
Calc'd: C, 40.71; H, 2.99; N, 5.93.
Found: C, 40.43, H, 2.71; N, 5.62.
(2f) 1-(2-Chloroethoxy)-4-chloro-3-nitrobenzene Method B To a 2L 3-neck round-bottom flask was added 4-chloro-3-nitro-phenol (50 g, 0.29 mol), potassium carbonate (100 g, 0.72 mol), dichloroethane (315 g, 3.2 mol), potassium iodide (5 g) and 2-butanone (1 L). The mixture was mechanically stirred and heated to reflux for 44 hours then allowed to cool to room temperature and the solids were filtered. The solvent was evaporated under vacuum and the oil dissolved in diethyl ether (300 mL) and washed with 10% sodium hydroxide. The organic layer was dried over anhydrous magnesium sulfate, filtered, and the solvent removed under vacuum. The product was dissolved in 1:1 methylene chloride-hexanes and filtered through silica. Upon concentration 54.5 g (78.% %) of product was afforded as a white solid: mp 44.5–46° C.
Elemental analysis for $C_8H_7Cl_2NO_3$
Calc'd: C, 40.71; H, 2.99; N, 5.93.
Found: C, 40.89, H, 2.70; N, 5.83.

Intermediate 3

7-Chloro-4-(2-chloroethoxy)-1H-indole

To a solution of 1-(2-chloroethoxy)-4-chloro-3-nitrobenzene (10.00 g, 0.04236 mol) in THF (230 mL) stirred in a cold bath at −50 to −40° C. was added a THF solution of vinylmagnesium bromide (132 mL, 1.0 M, 0.132 mol) over 2 minutes. After stirring in the cold bath for 2–2.5 hours, saturated NH$_4$Cl (150 mL) was added to the cold solution and it was removed from the cold bath. Enough 1 M HCl was added to dissolve the precipitated solids. This two phase system was stirred for 0.5 hour at most. The layers were separated and the aqueous phase was extracted once with Et$_2$O. Combination of the Et$_2$O and THF followed by drying over MgSO$_4$ and evaporation gave 15.43 g of a dark oil. This was purified by chromatography on silica gel using a three component elutant which consisted of 80% CH$_2$Cl$_2$ and 20% of a gradient of EtOAc/hexane. This gave the product as a yellow solid: 3.32 g (34%); mp 68–72° C. MS EI m/e 229, 231, 233 (M+); $^1$H NMR (400 MHz, DMSO-$d_6$) δ 3.99 (t, 2H, J=5.1 Hz), 4.34 (t, 2H, J=5.0 Hz), 6.51 (t, 1H, J=2.7 Hz), 6.53 (d, 1H, J=7.8 Hz), 7.04 (d, 1H, J=8.0 Hz), 7.29 (t, 1H, J=2.7 Hz), 11.43 (s, 1H).
Elemental analysis for $C_{10}H_9Cl_2NO$
Calc'd: C, 52.20; H, 3.94; N, 6.09.
Found: C, 52.09; H, 3.92; N, 5.96.

Intermediate 4

3.7-Dichloro-4-(2-chloroethoxy)-1H-indole

To a solution of 7-chloro-4-(2-chloroethoxy)-1H-indole (4.61 g, 20.0 mmol) in acetonitrile (100 mL) was added N-chlorosuccimide (2.94 g, 2.20 mmol) at room temperature. The reaction was allowed to stir for 1.5 hour then poured into water (100 mL) and extracted with methylene chloride (200 mL). The organic layer was dried over anhydrous magnesium sulfate, filtered, and the solvent removed under vacuum to afford a dark solid. This material was chromatographed (methylene chloride-hexanes: 1:2) to afford 4.15 g (78.4%) as a white solid: mp 106–107.5° C.; IR (KBr) 3400 cm-1; MS EI m/e 263, 265, 267, 269 (M+); $^1$H NMR (CDCl$_3$) δ 3.91 (2H, t, J=6.2 Hz), 4.33 (2H, t, J=6.2 Hz), 6.47 (1H, d, J=8.4 Hz), 7.08–7.13 (2H, m), 8.26 (1H, bs, NH).
Elemental analysis for $C_{22}H_{25}N_2O_3Cl$
Calc'd: C, 65.91; H, 6.28; N, 6.99
Found: C, 65.61; H, 6.21; N, 6.89

EXAMPLE 1

[2-(1 H-Indol-4-yloxy)-ethyl]-(4-phenyl-butyl)-amine

A solution of the 2-(1H-indol-4-yloxy)-chloroethane (1.80 g, 9.20 mmol) and 4-phenyl-1-aminobutane (4.12g, 27.6 mmol) in anhydrous dimethylsulfoxide (25 mL) was heated to 80° C. for 6 hours. The reaction mixture was poured into water (150 mL) and extracted with methylene chloride (3×100 mL). The organic layers were combined and dried over anhydrous magnesium sulfate, filtered, and the solvent concentrated. Purification by flash chromatography (5%–10% methanol-$CH_2Cl_2$) afforded 1.89 g (65.9%) of a tan oil: MS m/e 308 (M+). The oxalate salt was prepared in tetrahydrofuran: mp 202–204° C.

Elemental analysis for $C_{20}H_{24}N_2O \cdot C_2H_2O_4 \cdot 0.5H_2O$

Calc'd: C, 64.85; H, 6.68; N, 6.87.

Found: C, 64.66; H, 6.61; N, 6.70.

This general procedure utilizing 7-chloro-4-(2-chloroethoxy)-1H-indole or 3,7-dichloro-4-(2-chloroethoxy)-1H-indole and reacting with either benzylamine, 4-fluorobenzyl amine, 4-chlorobenzyl amine or thiophene-2-methylamine afforded:

(1b) Benzyl-[2-(7-chloro-1H-indol-4-yloxy)-ethyl]-amine (68%). The fumarate salt was prepared in isopropanol as colorless crystals; mp 168–170° C.; MS EI m/e 300, 302 (M+).

Elemental analysis for $C_{17}H_{17}ClN_2O \cdot 0.5C_4H_4O_4 \cdot 0.25C_3H_8O$ Calc'd: C, 63.45; H, 5.66; N, 7.49

Found: C, 63.12; H, 5.61; N, 7.31.

(1c) Benzyl-[2-(3,7-dichloro-1H-indol-4-yloxy)-ethyl]-amine (67.8%): The fumarate salt was prepared and characterized: mp 201–202° C.; MS EI m/e 334, 336, 338 (M+).

Elemental analysis for $C_{17}H_{16}Cl_2N_2O \cdot 0.5C_4H_4O_4$

Calc'd: C, 58.03; H, 4.61; N, 7.12.

Found: C, 57.88; H, 4.45; N, 6.96.

(1d) 4-Fluorobenzyl-[2-(3,7-dichloro-1H-indol-4-yloxy)-ethyl]-amine (64.5%): mp 102.5–103.5° C.

Elemental analysis for $C_{17}H_{15}FCl_2N_2O$

Calc'd: C, 57.81; H, 4.28; N, 7.93.

Found: C, 57.68; H, 4.16; N, 7.86.

(1e) 4-Chlorobenzyl-[2-(3,7-dichloro-1H-indol-4-yloxy)-ethyl]-amine (59.9%): mp 115–116° C.; MS EI 368 m/e (M+).

Elemental analysis for $C_{17}H_{15}Cl_3N_2O \cdot 0.25H_2O$

Calc'd: C, 54.57; H, 4.17; N, 7.49.

Found: C, 54.43; H, 3.82; N, 7.32.

(1f) Thien-2-ylmethyl-[2-(3,7-dichloro-1H-indol-4-yloxy)-ethyl]-amine (76.3%): mp 99–101° C., MS EI 340, 342, 344 m/e (M+).

Elemental analysis for $C_{15}H_{15}Cl_2N_2OS$

Calc'd: C, 52.70; H, 4.13; N, 8.21.

Found: C, 52.70; H, 3.95; N, 8.19.

Intemediate 5

N-Benzyl-N-[2-(1H-indol-3-(2,2,2-trifluoroethanoyl)-4-yloxy)-ethyl]-carbamic acid tert-butyl ester To a stirring anhydrous solution of benzyl-[2-(1H-indol-4-yloxy)-ethyl]-carbamic acid tert-butyl ester (1.85 g, 5.05 mmol) and TEA (0.8 mL, 0.6 g, 6 mmol) in $CH_2C_{12}$ was added trifluoroacetic acid anhydride (1.1 mL, 1.6 g, 7.8 mmol) over 5 minutes at room temperature. The reaction mixture was stirred at room temperature over-night. It was washed twice with $H_2O$ and then dried over $MgSO_4$. Evaporation of solvent gave 3.38g of residue. This was purified by chromatography on silica gel with a hexane/EtOAc gradient to give the title compound as an amorphous light yellow solid: 1.15g (49%); MS EI m/e 462 (M+); IR(KBr) 1719 $cm^{-1}$, 1744 $cm^{-1}$; $^1$H NMR (400 MHz, DMSO-$d_6$) δ 1.33 and 1.38 (2s, 9H, rotamers), 3.50–3.63 (2m, 2H, rotamers), 4.15 (t, 2H, J=5.5 Hz), 4.54 (s, 2H), 6.77 (d, 1H, J=7.9 Hz), 7.15 (d, 1H, J=8.1 Hz), 7.20–7.27 (m, 4H), 7.29–7.35 (m, 2H), 8.32 (s, 1H), 12.58 (s, 1H).

Intermediate 6

N -[2-(1H-indol-4-yloxy)-ethyl]-N-(4-phenyl-butyl)-trifluoroacetamide

To a solution of [2-(1H-indol-4-yloxy)-ethyl]-(4-phenyl-butyl)-amine (2.38 g, 7.72 mmol) and triethylamine (1.56 g, 15.4 mmol) in anhydrous methylene chloride (30 mL) at room temperature was slowly added trifluoroacetic anhydride (2.42 g, 11.6 mmol) over 10 minutes. The reaction was stirred for 1 hour and then poured into a 1:1 solution of saturated sodium carbonate-water (50 mL) and extracted with methylene chloride (2×100 mL). The organic layer dried over anhydrous magnesium sulfate, filtered, and the solvent evaporated. Purification by flash chromatography (20% ethyl acetate-hexanes) afforded 1.61 g (51.6%) of an off-white solid: mp 70–72° C.; MS m/e 404 (M+); IR (KBr) 3360, 2950, 1725 $cm^{-1}$.

Intermediates 7 & 8

N-Benzyl-N-[2-(7-chloro-1H-indol-4-yloxy)-ethyl]-2,2,2-trifluoro-acetamide and

N-Benzyl-N-[2-(7-chloro-3-trifluoroacetyl-1H-indol-4-yloxy)-ethyl]-2,2,2-trifluoro-acetamide To a solution of benzyl-[2-(7-chloro-1H-indol-4-yloxy)-ethyl]-amine (4.55 g, 15.1 mmol) in $CH_2Cl_2$ (200 mL) at room temperature was added triethylamine (TEA) (2.15 mL, 1.56 g, 15.4 mmol) and then trifluoroacetic acid anhydride (4.5 mL, 6.7 g, 32 mmol) over 20 minutes. The solution was stirred at room temperature over-night. It was washed twice with $H_2O$. Drying over $MgSO_4$ and evaporation of the solvent gave 7.33 g of residue which consisted primarily of the two products. These were separated and purified by chromatography on silica gel with a gradient of $CH_2Cl_2$/hexane/EtOAc (10/80/10, 4/82/14, 0/86/14, 0/80/20) which first eluted N-benzyl-N-[2-(7-chloro-1H-indol-4-yloxy)-ethyl]-2,2,2-trifluoro-acetamide as light yellow crystals: 2.79 g (47%);

mp 114–116° C.; MS EI m/e 396 (M+); IR (KBr) 1682 $cm^{-1}$; $^1$H NMR (400 MHz, CDCl$_3$) δ 3.79 and 3.86 (2t, 2H, J=5.6 Hz, J=5.0 Hz, rotamers), 4.28 and 4.31 (2t, 2H, J=5.6 Hz, J=5.0 Hz, rotamers), 4.89 and 4.93 (2s, 2H, rotamers), 6.38 and 6.40 (2d, 1H, J=8.3 Hz, J=8.5 Hz, rotamers), 6.64–6.68 (m, 1H), 7.05 and 7.08 (2d, 1H, J=8.1 Hz, J=8.3 Hz, rotamers); 7.19–7.44 (m, 6H), 8,42 (s, 1H).

Elemental analysis for $C_{19}H_{16}ClF_3N_2O_2$

Calc'd: C, 57.51; H, 4.06; N, 7.06.

Found: C, 57.11; H, 3.88; N, 7.01.

N-Benzyl-N-[2-(7-chloro-3-trifluoroacetyl-1H-indol-4-yloxy)-ethyl]-2,2,2-trifluoro-acetamide was then eluted off the column to afford 3.18 g (43%) of crystalline solid; mp 152–154° C.; MS FAB m/e 493 (MH+); IR (KBr) 1685 $cm^{-1}$, 1699 $cm^{-1}$; $^1$H NMR (400 MHz, CDCl$_3$) δ 3.84 and 4.01 (2t, 2H, J=5.0 Hz, J=5.3 Hz, rotamers), 4.26 and 4.31 (2t, 2H, J=5.5 Hz, J=5.0 Hz, rotamers), 4.92 and 5.00 (2s, 2H, rotamers), 6.63 and 6.66 (2d, 1H, J=8.8 Hz, J=8.8 Hz, rotamers), 7.27–7.42 (m, 6H), 8.04–8.08 (m, 1H), 9.13 (s, 1H).

Elemental analysis for $C_{21}H_{15}ClF_6N_2O_3$)

Calcd: C, 51.18; H, 3.07; N, 5.68.

Found: C, 51.31; H, 2.89; N, 5.58.

Intermediate 9

N-Benzyl-N-[2-(3-chloro-1H-indol-4-yloxy)-ethyl]-carbamic acid tert-butyl ester

To a solution of N-benzyl-N-[2-(1H-indol-4-yloxy)-ethyl]-carbamic acid tert-butyl ester (6.3 g, 17.2 mmol) in tetrahydrofuran (100 mL) was added N-chlorosuccinimide (2.3 g, 17.2 mmol) in two portions over 1 hour. The reaction was allowed to stir for 18 hours and the solvent removed under vacuum. The mixture was dissolved in diethyl ether and the insoluble solids filtered. The solvent was again removed and the product purified by chromatography (30% ethyl acetate-hexanes) to afford 5.65 g of white solid (81.9%): mp 114–116° C.

Elemental analysis for $C_{22}H_{25}N_2O_3Cl$

Calc'd: C, 65.91; H, 6.28; N, 6.99

Found: C, 65.61; H, 6.21; N, 6.89

This general procedure utilizing N-methyl-N-[2-(1H-indol-4-yloxy)-ethyl]-carbamic acid tert-butyl ester, N-[2-(1H-Indol-4-yloxy)-ethyl]-phthalimide, N-benzyl-N-[2-(7-chloro-1H-indol-4-yloxy)-ethyl]-2,2,2-trifluoro-acetamide and [2-(1H-indol-4-yloxy)-ethyl]-(4-phenyl-butyl)-trifluoroacetamide afforded, respectively:

(9b) N-Methyl-N-[2-(3-chloro-1H-indol-4-yloxy)-ethyl]-carbamic acid tert-butyl ester as a white solid: (74.9%); mp 153–154° C.; MS FAB m/z 325 (M$^+$+H$^+$).

Elemental analysis for $C_{16}H_{21}N_2O_3Cl$

Calc'd C, 59.17; H, 6.52; N, 8.62

Found C, 59.08; H, 6.33; N, 8.49

(9c) N-[2-(3-Chloro-1H-indol-4-yloxy)-ethyl]-phthalimide as yellowish white crystals: mp 161–163° C.

Elemental analysis for $C_{18}H_{13}N_2O_3.0.33H_2O$

Calc'd: C, 62.36; H, 3.97; N, 8.08

Found: C, 62.37; H, 3.68; N, 8.07

(9d) N-Benzyl-N-[2-(3,7-dichloro-1H-indol-4-yloxy)-ethyl]-2,2,2-trifluoro -acetamide as a white solid: (82%); mp 156–158° C.; MS EI m/e 430, 432, 434 (M$^+$); IR(KBr) 1680 cm$^{-1}$; $^1$H NMR (400 MHz, CDCl$_3$) δ 3.76 and 3.81 (2t, 2H, J=1.3 Hz, J=1.4 Hz, rotamers), 4.14 and 4.15 (2t, 2H, J=1.5 Hz, J=1.6 Hz, rotamers), 4.95 and 4.96 (2s, 2H, rotamers), 6.41 and 6.43 (2d, 1H, J=8.4 Hz, J=8.7 Hz, rotamers), 7.095 and 7.097 (2d, 1H, J=8.2 Hz, J=8.2 Hz, rotamers), 7.16 (d, 1H, J=2.5 Hz), 7.22–7.41 (m, 5H), 8.27–8.35 (m, 1H).

Elemental analysis for $C_{19}H_{15}Cl_2F_3N_2O_2$

Calc'd: C, 52.92; H, 3.51; N, 6.50

Found: C, 52.54; H, 3.26; N, 6.29

(9e) N-[2-(3-chloro-1H-indol-4-yloxy)-ethyl]-N-(4-phenyl-butyl)-trifluoroacetamide: (71.4%), mp 113–114° C.; MS m/e 438 (M+).

Elemental analysis for $C_{22}H_{22}N_2O_2ClF_3$

Calc'd: C, 60.21; H, 5.05; N, 6.38

Found: C, 60.51; H, 4.94; N, 6.31.

EXAMPLE 2

[2-(3-Chloro-1H-indol-4-yloxy)-ethyl]-(4-phenyl-butyl)-amine

A mixture of [2-(3-chloro-1H-indol-4-yloxy)-ethyl]-(4-phenyl-butyl)-trifluoroacetamide(1.15 g, 2.62 mmol) and potassium carbonate (2.53 g, mmol) in a solution of methanol-water (50 mL:3 mL) was heated to reflux for 3 hours. The solvent was removed under vacuum and the crude product was dissolved in methylene chloride (150 mL) and washed with water (100 mL). The aqueous layer was extracted again with methylene chloride (100 mL) and the combined organic layers dried over anhydrous magnesium sulfate, filtered, and the solvent evaporated. The product was purified by flash chromatography (5% methanol-methylene chloride) to afford 847 mg (94.3%) of a tan oil: MS m/e 342 (M+), 344 (M+). The fumarate salt was prepared in isopropanol: mp 195–196° C.

Elemental analysis for $C_{20}H_{23}N_2OCl.0.5C_4H_4O_4$

Calc'd: C, 65.91; H, 6.29; N, 6.99

Found: C, 66.15; H, 6.38; N, 6.81.

This general procedure utilizing N-benzyl-N-[2-(3,7-dichloro-1H-indol-4-yloxy)-ethyl]-2,2,2-trifluoro-acetamide, and N-benzyl-N-[2-(7-chloro-1H-indol-4-yloxy)-ethyl]-2,2,2-trifluoro-acetamide afforded, respectively:

(2b) Benzyl-[2-(3,7-dichloro-1H-indol-4-yloxy)-ethyl]-amine, 92%. The fumarate salt was prepared from ethanol as a white powder; mp 201–202° C.; MS EI m/e 334, 36, 338 (M$^+$).

Elemental analysis for $C_{17}H_{16}Cl_2N_2O.0.5C_4H_4O_4$

Calc'd: C, 58.03; H, 4.61; N, 7.12.

Found: C, 57.88; H, 4.45; N, 6.96.

(2c) 1 -[4-(2-Benzylamino-ethoxy)-7-chloro-1H-indol-3-yl]-2,2,2-trifluoro-ethanone: (80%). The fumarate salt was prepared in ethanol: mp 215° C. (dec); MS FAB m/e 397 (MH$^+$).

Elemental analysis for $C_{19}H_{16}ClF_3N_2O_2.0.5C_4H_4O_4$

Calc'd: C, 55.46; H, 3.99; N, 6.16.

Found: C, 55.24; H, 3.80; N, 6.08.

EXAMPLE 3

1-[4-(2-Benzylamino-ethoxy)-1H-indol-3-yl]-2,2,2-trifluoro-ethanone

To a solution of N-benzyl-N-[2-(1H-indol-3-(2,2,2-trifluoroethanoyl)-4-yloxy)-ethyl]-carbamic acid tert-butyl ester (1.1 g, 2.4 mmol) in methylene chloride (60 mL) was added trifluoroacetic acid (TFA) (0.21 g, 1.8 mmol). Thin layer chromatography (TLC) (CH$_2$Cl$_2$/CH$_3$OH, 88/12 v/v) showed no change after 1 hour at room temperature. TFA (0.74 g, 6.5 mmol) was added and the mixture stirred 2 hours. Some product was then visible in the TLC. TFA (0.86 g, 7.5 mmol) was added and the mixture was stirred overnight. TLC showed some starting material. TFA (0.06 g, 0.5 mmol) was added and the mixture was stirred for 1 hour. The reaction mixture was washed once with saturated NaHCO$_3$ (30–40 mL). It was dried over MgSO$_4$. Evaporation of the solvent gave 1.02 g of residue. This was purified by chromatography on silica gel with a gradient of CH$_2$Cl$_2$/CH$_3$OH (96/4 and 95/5) to give the product as a light tan oil (0.78 g, 90%).

To a hot solution of fumaric acid (0.2557 g, 2.203 mmol) in EtOH (15 mL) was added a hot solution of the base in EtOH (15 mL). This mixture stood at room temperature for 2 hours. It was filtered to give the title compound as a white powder: 0.5398 g (54%); decomp. >220° C.; MS EI m/e 362 (M$^+$); IR (KBr) 1660 cm$^{-1}$.

Elemental analysis for $C_{19}H_{17}F_3N_2O_2.0.5C_4H_4O_4$

Calc'd: C, 60.00; H, 4.56; N, 6.66.

Found: C, 60.12; H, 4.40; N, 6.75.

This general procedure utilizing benzyl-[2-(1H-indol-4-yloxy)-ethyl]-carbamic acid tert-butyl ester afforded (3b) N-Benzyl-[2-(1H-indol-4-yloxy)]-ethylamine, (26%). The fumarate salt was prepared in isopropanol: mp 158–165° C.

Elemental analysis for $C_{17}H_{18}N_2O \cdot C_4H_4O_4$
Calc'd: C, 65.96; H, 5.80; N, 7.33.
Found: C, 65.94; H, 5.87; N, 7.19.

Affinity for the dopamine autoreceptor was established by a modification of the standard experimental test procedure of Seemen and Schaus, European Journal of Pharmacology 203, 105–109 (1991), wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

High affinity for the serotonin 5-$HT_{1A}$ receptor was established by testing the claimed compound's ability to displace [$^3$H] 8-OHDPAT (dipropylaminotetralin) from the 5-$HT_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the 5-$HT_{1A}$ serotonin receptor subtype. The anxiolytic activity of buspirone is believed to be, at least partially, due to its 5-$HT_{1A}$ receptor affinity (Vander Maclen et al., Eur. J. Pharmacol. 1986, 129 (1–2) 133–130).

The results of these standard experimental test procedures were as follows:

| Example No. | $IC_{50}$ (nM) $D_2$ Quin. | $IC_{50}$ (nM) $D_2$ Spiper | $IC_{50}$ (nM) 5-$HT_{1A}$ | Ratio ant/agonist |
|---|---|---|---|---|
| (1a) | 10.5 | 184 | 0.71 | 18 |
| (1b) | 14.9 | 183 | 386 | 12 |
| (1c) | 13.6 | 284 | 438 | 21 |
| (1f) | 22.5 | 405 | — | 18 |
| (2a) | 9.55 | 193 | 0.99 | 20 |
| (2b) | 13.6 | 284 | 438 | 21 |
| (2c) | 54.8 | 449 | 102 | 8 |
| (3a) | 5.93 | 286 | 60 | 48 |
| (3b) | 19.4 | 501 | 36 | 26 |

Hence, the compounds of this invention effect the synthesis of the neurotransmitter dopamine and thus are useful in the treatment of dopaminergic disorders such as schizophrenia, Parkinson's disease, Tourette's Syndrome, alcohol addiction, cocaine addiction, and addiction to analagous drugs. These compounds also have affinity for the 5-$HT_{1A}$ receptors and therefore have the ability to modulate serotinergic activity. As such, they are also useful in the treatment of diseases characterized by disturbances in the serotinergic systems, such as anxiety, stress, depression, sexual dysfunctions and sleep disturbances.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be in either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of formula I

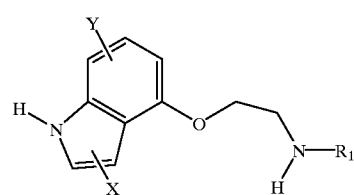

in which:
$R_1$ is alkyl of 1 to 10 carbon atoms, monocyclic cycloalkylalkyl of 6 to 12 carbon atoms, arylalkyl of 7 to 12 carbon atoms, (haloaryl)alkyl of 7 to 12 carbon atoms, (alkoxyaryl)alkyl of 8 to 12 carbon atoms, alkylphenyl of 7 to 12 carbon atoms, or 4-fluorobutyrophenone;

X is hydrogen, halogen, cyano, alkyl of 1 to 6 carbon atoms, acetyl, trifluoroacetyl, trifluoromethyl or formyl;

Y is hydrogen, halogen, alkoxy of 1 to 6 carbon atoms or alkyl of 1 to 6 carbon atoms; or a pharmaceutically acceptable salt thereof.

2. A compound of claim 1 in which:

$R_1$ is alkyl of 1 to 10 carbon atoms, cyclohexylmethyl, arylalkyl of 7 to 12 carbon atoms, (haloaryl)alkyl of 7 to 12 carbon atoms or (alkoxyaryl)alkyl of 8 to 12 carbon atoms;

X is H, halogen, cyano, alkyl of 1 to 6 carbon atoms, acetyl, trifluoroacetyl, trifluoromethyl or formyl;

Y is hydrogen, halogen, alkoxy of 1 to 6 carbon atoms or alkyl of 1 to 6 carbon atoms;

or a pharmaceutically acceptable salt thereof.

3. A compound of claim 1 in which $R_1$ is alkyl of 1 to 6 carbon atoms, benzyl, halobenzyl, alkoxybenzyl of 8 to 12 carbon atoms or alkylbenzyl of 8 to 12 carbon atoms; X is hydrogen, halogen or trifluoroacetyl and Y is hydrogen or halogen; or a pharmaceutically acceptable salt thereof.

4. The compound of claim 1 which is [2-(1H-indol-4-yloxy)-ethyl]-(4-phenyl-butyl)-amine or a pharmaceutically acceptable salt thereof.

5. The compound of claim 1 which is benzyl-[2-(7-chloro-1H-indol-4-yloxy)-ethyl]-amine or a pharmaceutically acceptable salt thereof.

6. The compound of claim 1 which is benzyl-[2-(3,7-dichloro-1H-indol-4-yloxy)-ethyl]-amine or a pharmaceutically acceptable salt thereof.

7. The compound of claim 1 which is 4-fluorobenzyl-[2-(3,7-dichloro-1H-indol-4-yloxy)-ethyl]-amine or a pharmaceutically acceptable salt thereof.

8. The compound of claim 1 which is 4-chlorobenzyl-[2-(3,7-dichloro-1H-indol-4-yloxy)-ethyl]-amine or a pharmaceutically acceptable salt thereof.

9. The compound of claim 1 which is [2-(3-chloro-1H-indol-4-yloxy)-ethyl]-(4-phenyl-butyl)-amine or a pharmaceutically acceptable salt thereof.

10. The compound of claim 1 which is 1-[4-(2-benzylamino-ethoxy)-7-chloro-1H-indol-3-yl]-2,2,2-trifluoro-ethanone or a pharmaceutically acceptable salt thereof.

11. The compound of claim 1 which is 1-[4-(2-benzylamino-ethoxy)-1H-indol-3-yl]-2,2,2-trifluoro-ethanone or a pharmaceutically acceptable salt thereof.

12. The compound of claim 1 which is (N-benzyl-[2-(1H-indol-4-yloxy)]-ethylamine
or a pharmaceutically acceptable salt thereof.

13. A pharmaceutical composition of matter comprising a compound of the formula:

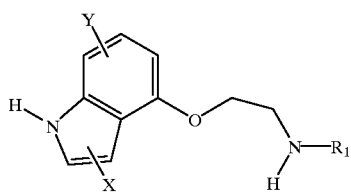

in which:

$R_1$ is alkyl of 1 to 10 carbon atoms, monocyclic cycloalkylalkyl of 6 to 12 carbon atoms, arylalkyl of 7 to 12 carbon atoms, (haloaryl)alkyl of 7 to 12 carbon atoms, (alkoxyaryl)alkyl of 8 to 12 carbon atoms, alkylphenyl of 7 to 12 carbon atoms, or 4-fluorobutyrophenone;

X is hydrogen, halogen, cyano, alkyl of 1 to 6 carbon atoms, acetyl, trifluoroacetyl, trifluoromethyl or formyl;

Y is hydrogen, halogen, alkoxy of 1 to 6 carbon atoms or alkyl of 1 to 6 carbon atoms;

or a pharmaceutically acceptable salt thereof and a pharmaceutically acceptable carrier therefor.

14. A method for reducing dopamine synthesis and release in a patient suffering from hyperactivity of the dopaminergic systems, which comprises administering to said patient a compound of the formula:

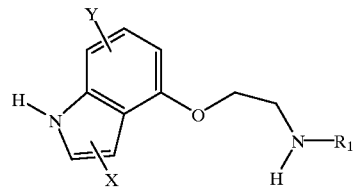

in which:

$R_1$ is alkyl of 1 to 10 carbon atoms, monocyclic cycloalkylalkyl of 6 to 12 carbon atoms, arylalkyl of 7 to 12 carbon atoms, (haloaryl)alkyl of 7 to 12 carbon atoms, (alkoxyaryl)alkyl of 8 to 12 carbon atoms, alkylphenyl of 7 to 12 carbon atoms, or 4-fluorobutyrophenone;

X is hydrogen, halogen, cyano, alkyl of 1 to 6 carbon atoms, acetyl, trifluoroacetyl, trifluoromethyl or formyl;

Y is hydrogen, halogen, alkoxy of 1 to 6 carbon atoms or alkyl of 1 to 6 carbon atoms;

or a pharmaceutically acceptable salt thereof, in an amount sufficient to modulate the dopamine systems of the brain.

15. A method for treating schizophrenia which comprises administering to a patient suffering from schizophrenia, orally or parenterally, a compound of the formula:

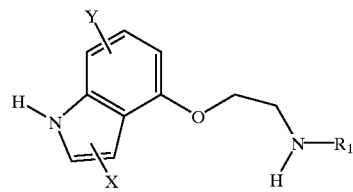

in which:

$R_1$ is alkyl of 1 to 10 carbon atoms, monocyclic cycloalkylalkyl of 6 to 12 carbon atoms, arylalkyl of 7 to 12 carbon atoms, (haloaryl)alkyl of 7 to 12 carbon atoms, (alkoxyaryl)alkyl of 8 to 12 carbon atoms, alkylphenyl of 7 to 12 carbon atoms, or 4-fluorobutyrophenone;

X is hydrogen, halogen, cyano, alkyl of 1 to 6 carbon atoms, acetyl, trifluoroacetyl, trifluoromethyl or formyl;

Y is hydrogen, halogen, alkoxy of 1 to 6 carbon atoms or alkyl of 1 to 6 carbon atoms;

or a pharmaceutically acceptable salt thereof, in an amount sufficient to alleviate the symptoms of schizophrenia.

* * * * *